(12) United States Patent
Blume et al.

(10) Patent No.: US 6,683,197 B1
(45) Date of Patent: Jan. 27, 2004

(54) PROCESS FOR THE PRODUCTION OF 4,4-DIMETHYL-5αA-CHOLESTA-8,14,24-TRIEN-3β-01 AND INTERMEDIATE PRODUCTS IN PROCESS (I)

(75) Inventors: Thorsten Blume, Berlin (DE); Peter Esperling, Berlin (DE); Joachim Kuhnke, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 472 days.

(21) Appl. No.: 09/288,691

(22) Filed: Apr. 9, 1999

Related U.S. Application Data
(60) Provisional application No. 60/089,018, filed on Jun. 12, 1998.

(30) Foreign Application Priority Data

Apr. 9, 1998 (DE) .......................................... 198 17 520
May 20, 1998 (DE) .......................................... 198 23 677

(51) Int. Cl.$^7$ ................ C07J 9/00; C07J 5/00
(52) U.S. Cl. ...................... 552/544; 552/600
(58) Field of Search .................. 552/544, 600

(56) References Cited

PUBLICATIONS

Ruan, B. et al., "An Alternative Synthesis Of 4,4–Dimethyl–5α–Cholesta–8,14,24–Trien–3β–01, An intermediate In Sterol Biosynthesis And A Reported Activator Of Meiosis And Of Nuclear Orphan Receptor LXRα," Biorganic & Medicinal Chemistry Letters, Bd. 8, Nr. 3, pp. 233–236, Feb. 3, 1998.

Dolle, R.E., et al., "Synthesis Of Zymosterol, Fecosterol, And Related Biosynthetic Sterol Intermediates", Journal of the American Chemical Society, Bd. 111, Nr. 1, pp. 278–284, Jan. 4, 1989.

R.B. Woodward et al., "The Synthesis Of Lanosterol (Lanostadienol)," Journal of the Chemical Society, Nr. 3, pp. 1131–1144, Mar. 1957.

R.E. Dolle et al., "Improved Preparation of (3β,5α, 14α)–3–Hydroxy–14–methy1cholest–7–en–15–one. Synthesis Of Ergostenone And 20α–(Hydroxymethyl)pregnenone Analogues," Journal of Organic Chemistry, Bd. 51, Nr. 21, pp. 4047–4053, Oct. 17, 1986.

J. van der Eycken et al., "24(R),25–Dihydroxycholesterol; An Attempt For Side Chain Stereocontrol Via Iodolactonization," Bull. Soc. Chim. Belg. vol. 95/n°, pp. 289–292, Apr. 1986.

*Primary Examiner*—Barbara P. Badio
(74) *Attorney, Agent, or Firm*—Millen, White, Zelano & Branigan, P. C.

(57) ABSTRACT

The subject of this invention is a new process with variant embodiments for the production of compound 1.

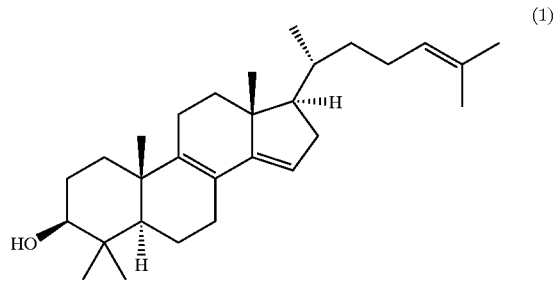

6 Claims, No Drawings

PROCESS FOR THE PRODUCTION OF 4,4-DIMETHYL-5αA-CHOLESTA-8,14,24-TRIEN-3β-01 AND INTERMEDIATE PRODUCTS IN PROCESS (I)

This application claims the benefit of U.S. Provisional Application No. 60/089,078 filed Jun. 12, 1998.

The invention relates to a process for the production of 4,4-dimethyl-5α-cholesta-8,14,24-trien-3β-ol (1) and intermediate products in the process

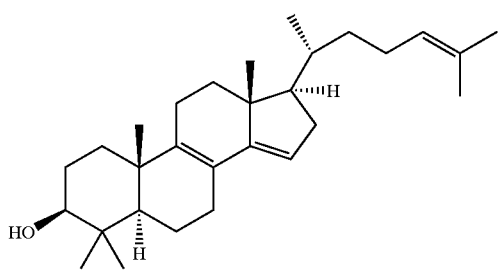

(1)

Studies by Byskov et al. (Nature 1995, 374, 559) show that 4,4-dimethyl-5α-cholesta-8,14,24-trien-3β-ol, formula I, named FF-MAS below, isolated from human follicular fluid, is an endogenous substance that regulates meiosis, to which advantageous hormonal effects are attributed. This substance is thus of importance for pharmaceutical applications, for example to promote fertility.

A first synthesis of this natural substance, which will take place in the biosynthesis of cholesterol from lanosterol, was described by Dolle et al. (J. Am. Chem. Soc. 1989, 111, 278). Starting from ergosterol, FF-MAS is obtained in an 18-step synthesis sequence at great cost. Large parts of the synthesis are dedicated to the partial chemical degradation of the ergosterol side chain, the subsequent creation of the FF-MAS side chain and the protective group chemistry that is necessary to achieve this goal.

A second synthesis of FF-MAS was described by Schroepfer et al. starting from dehydrocholesterol in a 13-step synthesis (Bioorg. Med. Chem. Lett. 1997, 8, 233). Also in this synthesis, a more expensive protection of the diene system must be performed in the side chain degradation. only four steps (epoxidation and rearrangement for protection; reduction and elimination for the regeneration of the diene system) are due to the protective group strategy.

The objects of this invention are new processes for the synthesis of FF-MAS. The subjects of this invention are also the new, previously unknown compounds that are processed within the framework of the syntheses and can be used per se or derivatized as starting materials for the synthesis of other target molecules, for example for the synthesis of FF-MAS analogues (see WO 96/00235) and the use of compounds for the production of 4,4-dimethyl-5α-cholesta-8,14,24-trien-3β-ol.

This object is achieved by the teaching of the claims.

By the two processes according to the invention, considerably fewer intermediate steps take place than within the known syntheses of Dolle et al. The number of purification steps is considerably lower, and no technically complex devices, such as an ozone generator with the facilities that are necessary for its operation, are required.

Process Variant 1

According to Diagram 1, FF-MAS is produced in a ten-step sequence starting from, for example, 3-oxopregn-4-enoic-21-acid methyl ester (Formula 2 with $R^1$=$CH_3$) (Helv. Chim. Acta 1939, 22, 1178 and 1184). The compound that is mentioned here as educt is readily accessible in various ways from commercially available steroids. For example, the production of a compound of formula 2 with $R^1$=$CH_3$ in a three-step sequence from 3β-hydroxyandrost-5-en-17-one (CAS Registry Number 53-43-0; 571-35-7, etc.) via Horner-Wittig (e.g., Synth. Commun. 1977, 7, 215), reduction of the resulting 17-double bond (e.g., Synthesis 1996, 455) and subsequent Oppenauer oxidation (e.g., Helv. Chim. Acta 1939, 22, 1178 and 1884) are described.

Starting from 3β-acetoxy-androst-5-en-17-one (CAS Registry Number 853-23-6, etc.), a compound of formula 2, with $R^1$=$CH_3$, can also be produced via condensation with malodinitrile, subsequent reduction of the resulting 17,20-double bond with sodium borohydride, nitrile saponification and decarboxylation with potassium hydroxide in ethylene glycol, esterification of the resulting carboxylic acid (Coll. Czech. Chem. Commun. 1982, 1240) and final Oppenauer oxidation (e.g., Helv. Chim. Acta 1939, 22, 1178 and 1184).

It is familiar to one skilled in the art that $R^1$ can be varied in compounds of formula 2 according to standard methods. This can happen by using other alcohols in the esterification step, but also by reesterification of an already present ester. $R^1$ can thus have the meaning of hydrogen, methyl, ethyl, propyl, isopropyl, butyl and the corresponding butyl isomers, pentyl and the corresponding pentyl isomers as well as hexyl and the corresponding hexyl isomers, phenyl, benzyl, ortho-, meta- and para-methyl phenyl.

The reaction of a compound of formula 2 to a compound of formula 3 is carried out according to processes that are known in the art (e.g., Helv. Chim. Acta 1980, 63, 1554, J. Am. Chem. Soc. 1954, 76, 2852). For example, a compound of formula 2 is reacted in the presence of bases such as, for example, the alkali salts of lower alcohols, but preferably potassium tert-butylate, with an alkylating agent such as, for example, dimethyl sulfate, dimethyl carbonate or else methyl iodide in a solvent or solvent mixture. As solvents, lower, preferably tertiary alcohols as well as ethers, for example methyl tert-butyl ether or tetrahydrofuran and their mixtures can be used. The use of tert-butanol or a mixture of tert-butanol and tetrahydrofuran is preferred. The reaction is performed in a temperature range of 0° C. to 65° C., but preferably in a temperature range of 15° C. to 50° C.

The reaction of a ketone of formula 3 to the corresponding 3-alcohol of formula 4 can be performed with a considerable number of reducing agents. As examples, there can be mentioned: $BH_3$ complexes (e.g., with tert-butylamine or trimethylamine), selectrides, sodium and lithium borohydride, inhibited lithium aluminum hydrides (e.g., LiAl (O'Bu)$_3$H); microorganisms such as, e.g., baker's yeasts or enzymes, for example, 3β-hydroxy steroid dehydrogenase, can also be used.

It is known to one skilled in the art that depending on the reagent that is used, various solvents or solvent mixtures and reaction temperatures can be used. Preferred here, however, are borohydrides, such as, for example, sodium borohydride in suitable solvents, such as, for example, lower alcohols or mixtures of alcohols with aprotic solvents, for example dichloromethane or tetrahydrofuran. The reactions are performed in a temperature range of −20° C. to 40° C., but preferably in the range of 0° C. to 30° C.

Before the introduction of the 7,8-double bond (5→6), the 3-OH group of a compound of formula 4 is provided with a protective group $R^2$ that is suitable for this reaction. As protective groups, for example, esters of aliphatic and aromatic carboxylic acids, e.g., acetic- and benzoic acid esters, acetal protective groups, such as, for example, tetrahydropyranyl-, methoxymethyl- or methoxyethoxymethyl ethers, but also other ether protective groups, for example, silyl ethers, such as, for example, trimethylsilyl-, triethylsilyl- or triisopropylsilyl; triphenylsilyl; dimethyl(1, 1-dimethylethyl)silyl-ether, are suitable.

Depending on the desired protective group, the reaction conditions and reaction temperatures vary. The introduction of the respective protective group is carried out according to processes that are known to one skilled in the art. As an example, the esterification of a compound of formula 4 with acetyl chloride in the presence of a base such as triethylamine or pyridine with or even without the addition of an inert solvent, for example dichloromethane in a temperature range of 0° C. to 60° C., can be mentioned. The introduction of a silyl protective group is carried out preferably by reaction of a compound of formula 4 with a silyl halide, but preferably dimethyl-(1,1-dimethylethyl)silyl-chloride or triethylsilyl chloride in the presence of a base, for example imidazole, in a suitable solvent such as, for example, dimethylformamide in a temperature range of 10° C. to 140° C., but preferably between 20° C. and 100° C. The introduction of the 7,8-double bond into a compound of formula 5 (→6) can be carried out in a two-step process. First, it is bromated in an allylic manner to the 5,6-double bond in the 7-position, and then a compound of formula 6 is obtained by eliminating the hydrogen bromide. The bromine compound does not need to be isolated, but can generally be used directly in the next step. The bromation is carried out according to processes that are known in the art. For example, N-bromosuccinimide can be used in a suitable solvent, such as, for example, benzene, lower alkanes or else halogenated hydrocarbons, such as, for example, carbon tetrachloride. The reaction can be performed with the addition of a radical starter, for example dibenzoyl peroxide, but also in the presence of light (see, e.g.: J. Org. Chem. 1949, 14, 433; Bull. Chem. Soc. Jpn. 1986, 59, 3702; Monatshefte Chem [Chem Monthly Publication] 1975, 106, 1415). Other bromation reagents can also be used; for example, N,N-dibromodimethylhydantoin can be mentioned. Usually, the reaction is performed in a suitable solvent, such as, for example, benzene, or a mixture of benzene and hexane at elevated temperature (see, e.g.: J. Med. Chem. 1977, 20, 5; J. Am. Chem. Soc. 1977, 99, 3432). For the bromation step, other solvents than those previously mentioned can also be used, for example, formic acid methyl ester (e.g.: Angew. Chem. [Applied Chemistry] 1980, 92, 471).

To cleave hydrogen bromide, various reagents can be used, preferably nitrogen bases such as, for example, quinaldine or collidine, but also other reagents, such as trimethylphosphite, are preferred. The reaction is performed in suitable solvents, for example in an aromatic hydrocarbon such as xylene in a temperature range of between 7° C. and 145° C. (see, e.g.: Helv. Chim. Acta 1973, 56, 1708; J. Org. Chem. 1951, 16, 1126: J. Org. Chem. 1982, 47, 2536).

The reaction of a compound of formula 5 to a compound of formula 6 can also be carried out by direct dehydrogenation in a reaction step, however. As dehydrogenating agents, quinones, for example 2-methyl-1,4-naphthoquinone (Recl. Trav. Chim. Pays Bas [The Netherlands] 1940, 59, 454) or 1,4-benzoquinone (J. Am. Chem. Soc. 1946, 68, 738) can be used. Preferred for the reaction of a compound of formula 5 to a compound of formula 6, however, are the two-step processes that consist of a bromation step and a subsequent dehydrobromation step.

The isomerization of a compound of formula 6 (→7) can be carried out according to various methods, for example hydrochloric acid can be used in a solvent mixture that consists of ethanol, benzene and water (J. Org. Chem. 1986, 51, 4047). Ethanol and methanol are also described as the only solvents for such diene-isomerizations, whereby hydrochloric acid is also used (e.g.: J. Am. Chem. Soc. 1953, 75, 4404; Tet. Lett. 1967, 3699). If the operation is performed according to one of the previously described methods, compounds of formula 7 are obtained, in which $R^2$ means hydrogen and $R^1$ means ethyl or methyl, depending on the alcohol used. The use of HCl gas in solvents such as chloroform or acetic acid is also described (e.g.: J. Org. Chem. 1988, 53, 1563: J. Chem. Soc. 1962, 2917). The isomerization can also be performed, however, with use of other acids and/or solvents, thus with p-toluenesulfonic acid in benzene (Chem. Pharm. Bull. 1988, 36, 2724).

The isomerization of the 5,7-diene can also be performed with sulfuric acid in solvents such as dioxane, primary alcohols or their mixtures with and without addition of aromatic hydrocarbons such as, for example, toluene at elevated temperature; here, the preferred temperature range reaches from 70° C. to 120° C., whereby the operation is optionally performed in a pressure vessel. In this case, a compound of formula 7, in which $R^2$ means hydrogen, and $R^1$ corresponds to the hydrocarbon portion of an optionally used alcohol, is obtained, and without the addition of alcohol, $R^1$ generally remains unchanged. In addition, the desired isomerization can also be performed in sulfur dioxide at elevated temperature in the pressure vessel (J. Chem. Soc. 1954, 814). Also described is the use of transition metal catalysts such as, for example, rhodium trichloride (J. Chem. Soc. Perkin I, 1977, 359).

The alkylation of a compound of formula 7 (→8) is preferably performed on those derivatives in which $R^1$ means methyl or ethyl and $R^2$ means hydrogen or a protective group, such as trialkylsilyl, tretrahydropyranyl, methoxymethyl or, for example, methoxyethoxymethyl. The desired protective group is optionally introduced before alkylation according to the methods that are known in the art to one skilled in the art. Alkylations of steroidal 20-carboxylic acid esters are described in various ways. Mainly the methyl or ethyl esters are used here. In addition to the frequently described introduction of a 20-methyl group, a number of alkylations with complex components are also described (see, for example, Bull. Soc. Chim. Belg. 1986, 95, 289; Tet. Lett. 1987, 28, 1685; J. Am. Chem. Soc 1995, 117, 1849; J. Chem. Soc. Chem. Comm., 1975, 968).

As an alkylating reagent, here the 5-bromo-2-methyl-2-pentene or the 5-iodo-2-methyl-2-pentene (e.g.: Synthesis 1979, 37) or a sulfonic acid ester, preferably the methanesulfonic acid ester or the p-toluenesulfonic acid ester of the corresponding carbinol 4-methyl-3-pentenol is used. For deprotonation of a compound of formula 7, various bases can be used. As examples, potassium and sodium hexamethyldisilazide (Tet. Lett. 1996, 37, 7473; Chem. Comm. 1997, 8, 765) and also other nitrogen bases, for example, lithium diisopropylamide (see, e.g., J. Chem. Soc. Perkin 1, 1978, 1282; Tet. Lett. 1996, 37, 9361) can be mentioned. Other lithium dialkylamide bases can also be used. Lithium diisopropylamide is preferred, however. With or even after addition of the alkylating agent, hexamethylphosphonic acid triamide or hexamethylphosphoric acid triamide can be added to the reaction. As solvents, aprotic solvents, preferably ethers such as, for example, diethyl ether or else tetrahydrofuran or their mixtures with hydrocarbons, e.g., hexane, are used. Tetrahydrofuran, however, is preferred here with or without the addition of hexane. The reaction is performed in a temperature range of −78° C. to room temperature, but preferably in a temperature range of −40° C. to 10° C.

Diagram 1

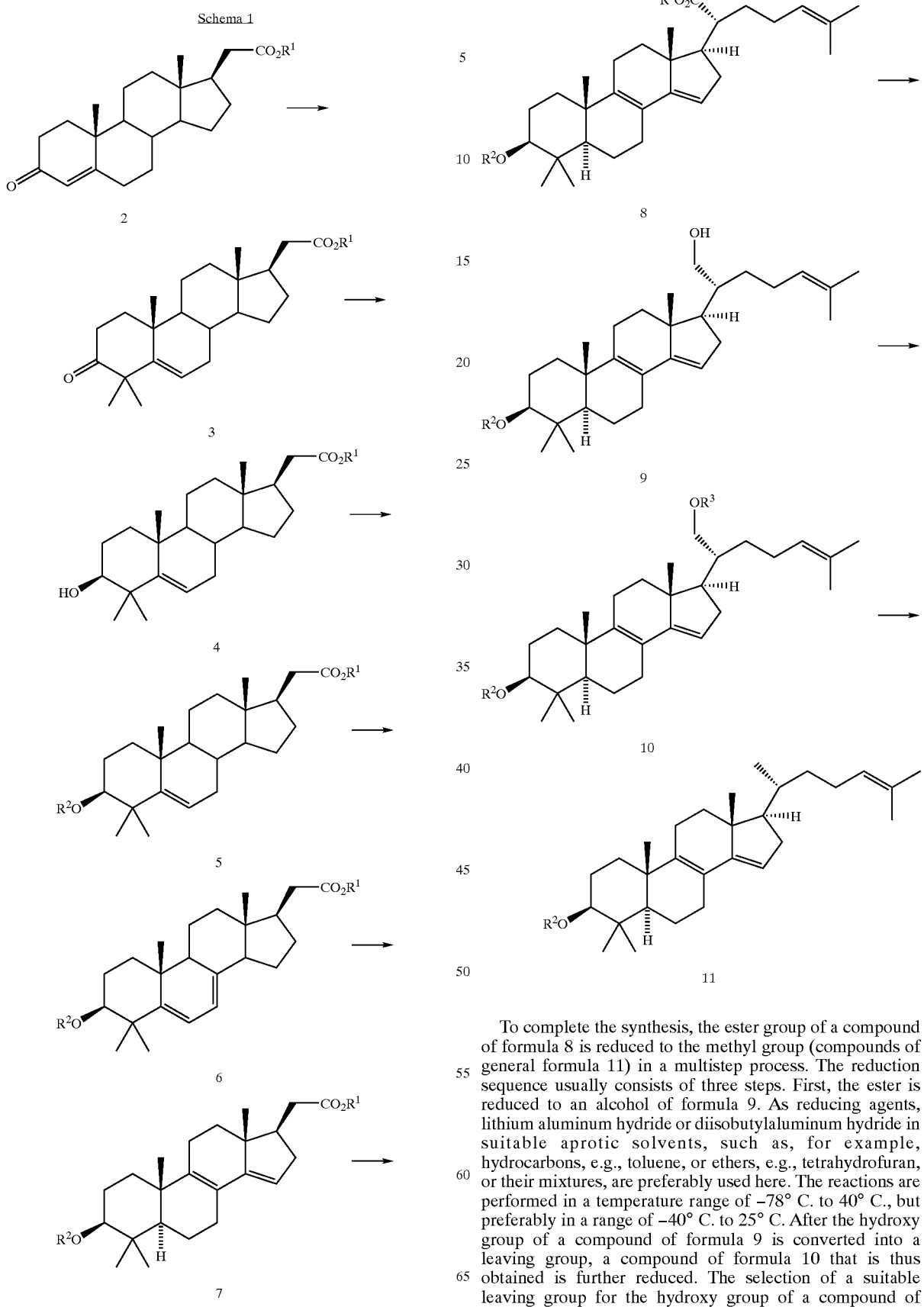

To complete the synthesis, the ester group of a compound of formula 8 is reduced to the methyl group (compounds of general formula 11) in a multistep process. The reduction sequence usually consists of three steps. First, the ester is reduced to an alcohol of formula 9. As reducing agents, lithium aluminum hydride or diisobutylaluminum hydride in suitable aprotic solvents, such as, for example, hydrocarbons, e.g., toluene, or ethers, e.g., tetrahydrofuran, or their mixtures, are preferably used here. The reactions are performed in a temperature range of −78° C. to 40° C., but preferably in a range of −40° C. to 25° C. After the hydroxy group of a compound of formula 9 is converted into a leaving group, a compound of formula 10 that is thus obtained is further reduced. The selection of a suitable leaving group for the hydroxy group of a compound of formula 10 depends on the nature of substituent $R^2$. If $R^2$ means hydrogen, a reagent must be selected, which ensures differentiation between the secondary hydroxyl group at C-3 and the primary hydroxyl group at C-21. For this purpose, especially reactive sulfonic acid derivatives are suitable as sterically exacting sulfonic acids, for example the anhydrides or acid halides of p-toluenesulfonic acid or the 2,4,6-trimethylbenzenesulfonic acid, which differentiate between primary and secondary hydroxyl groups. If R is one of the indicated protective groups, derivatives of other sulfonic acids, for example methanesulfonic acid chloride, can also be used. These esterifications are performed preferably in the presence of a base such as pyridine or aliphatic tertiary amines, for example triethylamine, which can be used as the only solvent. The reaction can also be performed, however, with the addition of a solvent, such as, for example, dichloromethane. Usually, the operation is performed here in a temperature range of 0° C. to 70° C. The reduction of a compound of formula 10 can be produced with the same reagents and under the same reaction conditions as described previously for the reduction of ester. As a reducing agent, in addition lithium triethyl borohydride can be mentioned here, which has proven itself especially well for the reductive removal of sulfonic acid esters. Examples of such multistep conversions of an ester into a methyl group are found in many literature citations, i.a., in: Tet. Lett. 1987, 28, 1685; J. Am. Chem. Soc. 1995, 117, 1849, etc.

Thus, FF-MAS (1), with $R^2$ meaning hydrogen, is obtained directly. If $R^2$ represents a protective group, however (see above), a compound of formula 11 is obtained, from which the protective group is cleaved according to the methods that are familiar to one skilled in the art.

Process Variant 2

In this process variant (cf. diagram 2), the isomerization step (5,7-diene→8,14-diene) is shifted to the synthesis end. The sequence of alkylation and reduction of the ester group (6→→15) is performed analogously to the methods that are described in process variant 1. The isomerization of a compound of formula 15 is also performed analogously to process variant 1. For $R^2$ meaning hydrogen, FF-MAS (1) is obtained directly. If $R^2$ represents a protective group (see above), and if the protective group in question remains unchanged under the reaction conditions that are used for the isomerization, not FF-MS (1), but rather a compound of formula 11, from which the protective group is cleaved according to the method that is familiar to one skilled in the art, is obtained directly.

Diagram 2

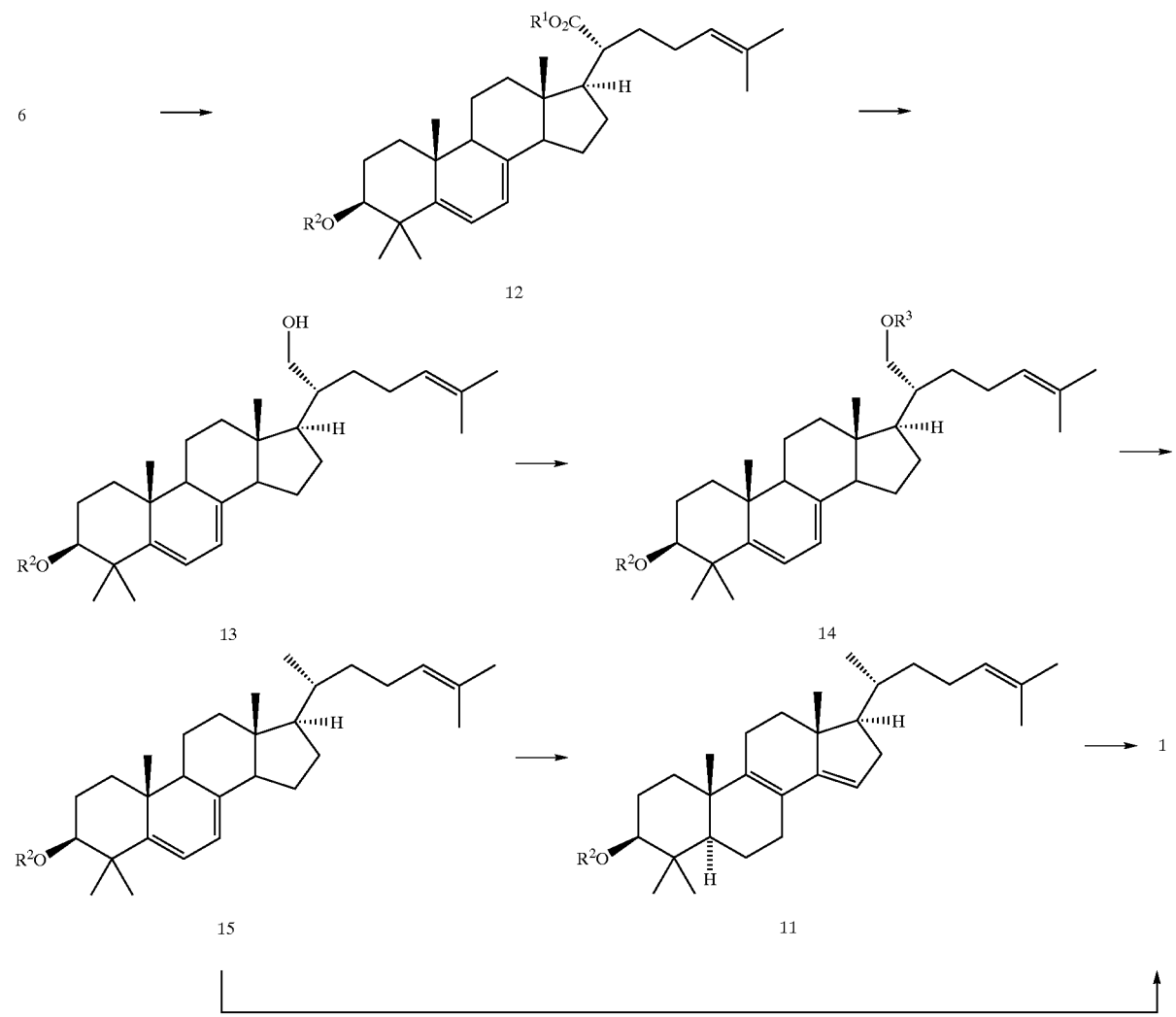

EXAMPLES

Example 1

(Process Variant 2)

a) 4,4-Dimethyl-3-oxopregn-5-enoic-21-acid methyl ester 143.2 g of 3-oxopregn-4-enoic-21-acid methyl ester, dissolved in one liter of tetrahydrofuran, is added at 45° C. to 186.6 g of potassium tert-butylate in one liter of tert-butanol. After 10 minutes, 183 ml of methyl iodide is added in drops. After another 50 minutes, it is poured onto 10 liters of ice water, acidified with 4N hydrochloric acid and extracted with ethyl acetate. After the organic phase is washed with water, sodium bicarbonate solution and saturated common salt solution, it is dried on sodium sulfate, filtered, concentrated by evaporation, and the evaporation residue is chromatographed on silica gel with a mixture of n-hexane and ethyl acetate. 75.1 g of 4,4-dimethyl-3-oxopregn-5-enoic-21-acid methyl ester is obtained.

$^1$H-NMR (CDCl$_3$): δ=0.62 ppm (s, 3H, H-18); 0.87 (s, 3H, H-19); 1.22 (s, 6H, 4-CH$_3$); 2.14 (dd, J=10 and 15 Hz, 1H, H-20); 2.39 (dd, J=5 and 15 Hz, 1H, H-20); 3.66 (s, 3H, CO$_2$—CH$_3$); 5.55 (m, 1H, H-6)

b) 4,4-Dimethyl-3β-hydroxypregn-5-enoic-21-acid methyl ester 74.5 g of the compound that is described in step a) is introduced into one liter of dichloromethane and mixed with 7.57 g of sodium borohydride. After 0.1 liter of methanol is added in drops, it is stirred for 4.5 hours. The reaction mixture is stirred into one liter of ice-cold 1N hydrochloric acid and then dispersed between ethyl acetate and water. After phase separation, washing of the organic phase with saturated common salt solution, drying on sodium sulfate, filtration and concentration by evaporation of the filtrate, 75.2 g of 4,4-dimethyl-3β-hydroxypregn-5-enoic-21-acid methyl ester is obtained, which is further used without purification.

$^1$H-NMR (CDCl$_3$): δ=0.60 ppm (s, 3H, H-18); 1.08 (s, 3H, 4-CH$_3$); 1.10 (s, 3H, 4-CH$_3$); 1.14 (s, 3H, H-19); 2.22 (dd, J=10 and 15 Hz, 1H, H-20); 2.38 (dd, J=5 and 15 Hz, 1H, H-20); 3.25 (m, 1H, H-3); 3.66 (s, 3H, CO$_2$—CH$_3$); 5.57 (m, 1H, H-6)

c) 4,4-Dimethyl-3β-[[dimethyl(1,1-dimethylethyl)silyl]oxy]pregn-5-enoic-21-acid methyl ester 74.7 g of the compound that is described in step b) is stirred with 40.8 g of imidazole and 60.3 g of tert-butyldimethylsilyl chloride in 1.25 liters of N,N-dimethylformamide for 20 hours at 40° C. Then, it is poured onto 10 liters of 0.5N hydrochloric acid and filtered off by suction. The filter cake is absorptively precipitated with four liters of 0.5N sodium hydroxide solution. After being filtered off by suction once again and after drying of the filter cake, 93.5 g of 4,4-dimethyl-3β-[[dimethyl(1,1-dimethylethyl)silyl]oxy]pregn-5-enoic-21-acid methyl ester is obtained, which is further used without purification.

$^1$H-NMR (CDCl$_3$): δ=0.03 ppm (s, 3H, Si—CH$_3$); 0.04 ppm (s, 3H, Si—CH$_3$); 0.61 ppm (s, 3H, H-18); 0.90 ppm (s, 9H, Si-$^t$Bu); 1.04 (s, 3H); 1.07 (s, 3H); 1.09 (s, 3H); 2.13 (dd, J=10 and 15 Hz, 1H, H-20); 2.38 (dd, J=5 and 15 Hz, 1H, H-20); 3.21 (dd, J=5 and 12 Hz, 1H, H-3); 3.67 (s, 3H, CO$_2$—CH$_3$); 5.55 (m, 1H, H-6)

d) 4,4-Dimethyl-3β-[[dimethyl(1,1-dimethylethyl)silyl]oxy]pregna-5,7-dienoic-21-acid methyl ester 93 g of the compound that is described in step c) is boiled with 32.6 g of 1,3-dibromo-5,5-dimethylhydantoin in a mixture of 0.75 liter of n-hexane and benzene each for 20 minutes. After cooling, it is suctioned off, the filtrate is concentrated by evaporation, and the evaporation residue is boiled for one hour with 45 ml of trimethylphosphite in 0.9 liter of xylene. After concentration by evaporation and chromatography on silica gel with a mixture of n-hexane and ethyl acetate, 86.35 g of 4,4-dimethyl-3β-[[dimethyl(1,1-dimethylethyl)silyl]oxy]pregna-5,7-dienoic-21-acid methyl ester is obtained.

$^1$H-NMR (CDCl$_3$): δ=0.02 ppm (s, 3H, Si—CH$_3$); 0.04 ppm (s, 3H, Si—CH$_3$); 0.50 ppm (s, 3H, H-18); 0.89 ppm (s, 9H, Si-$^t$Bu); 0.95 (s, 3H, H-19); 1.08 (s, 3H, 4-CH$_3$); 1.12 (s, 3H, 4-CH$_3$); 2.13 (dd, J=10 and 15 Hz, 1H, H-20); 2.40 (dd, J=5 and 15 Hz, 1H, H-20); 3.33 (dd, J=5 and 12 Hz, 1H, H-3); 3.66 (s, 3H, CO$_2$—CH$_3$); 5.52 (m, 1H, H-7); 5.89; (d, J=6 Hz, 1H, H-6)

e) 4,4-Dimethyl-3β-[[dimethyl(1,1-dimethylethyl)silyl]oxy]cholesta-5,7,24-trienoic-21-acid methyl ester 65 g of the compound that is described in step d), dissolved in 0.8 liter of tetrahydrofuran, is added in drops to a solution of 0.268 mol of lithium diisopropylamide, produced from 168 ml of a 1.6 molar solution of n-butyllithium in hexane and 45 ml of diisopropylamine in 90 ml of tetrahydrofuran at −30° C. After one hour, 56 g of 5-iodo-2-methyl-2-pentene in 75 ml of tetrahydrofuran is added at this temperature. Then, it is heated to 0° C. and left for 16 hours at this temperature.

After 0.1 liter of 1N hydrochloric acid is added, it is mixed with 1.5 liters of a mixture of hexane and ethyl acetate. After phase separation, the organic phase is washed with water and saturated common salt solution, dried on sodium sulfate and concentrated by evaporation. After coarse filtration on silica gel with hexane and dichloromethane as eluants, it is crystallized from a mixture of ethanol and tert-butyl methyl ether. 41 g of 4,4-dimethyl-3β-[[dimethyl(1,1-dimethylethyl)silyl]oxy]cholesta-5,7,24-trienoic-21-acid methyl ester is obtained.

$^1$H-NMR (CDCl$_3$): δ=0.04 ppm (s, 3H, Si—CH$_3$); 0.07 ppm (s, 3H, Si—CH$_3$); 0.61 ppm (s, 3H, H-18); 0.91 ppm (s, 9H, Si-$^t$Bu); 0.97 (s, 3H, H-19); 1.10 (s, 3H, 4-CH$_3$); 1.13 (s, 3H, 4-CH$_3$); 1.58 and 1.70 (1s br. each, in each case 3H, H-26 and H-27); 2.28 (m, 1H, H-20); 3.36 (dd, J=5 and 12 Hz, 1H, H-3); 3.68 (s, 3H, CO$_2$—CH$_3$); 5.08 (m, 1H, H-24); 5.53 (m, 1H, H-7); 5.90 (d, J=6 Hz, 1H, H-6)

f) 4,4-Dimethyl-3β-[[dimethyl(1,1-dimethylethyl)silyl]oxy]cholesta-5,7,24-trien-21-ol 40 g of the compound, described in step e), in 0.25 liter of tetrahydrofuran, is added in drops to 5.31 g of lithium aluminum hydride, suspended in 0.25 liter of tetrahydrofuran, at 0° C. After 3 hours of stirring at room temperature, it is mixed with 20 ml of saturated ammonium chloride solution while being cooled with ice. After 10 minutes, it is mixed with sodium sulfate and after another 5 minutes, it is suctioned off. After the filtrate is concentrated by evaporation, 37.57 g of 4,4-dimethyl-3β-[[dimethyl(1,1-dimethylethyl)silyl]oxy]cholesta-5,7,24-trien-21-ol is obtained.

$^1$H-NMR (CDCl$_3$): δ=0.04 ppm (s, 3H, Si—CH$_3$); 0.06 ppm (s, 3H, Si—CH$_3$); 0.61 ppm (s, 3H, H-18); 0.90 ppm (s, 9H, Si-$^t$Bu); 0.98 (s, 3H, H-19); 1.10 (s, 3H, 4-CH$_3$); 1.13 (s, 3H, 4-CH$_3$); 1.62 and 1.70 (1s br. each, in each case 3H, H-26 and H-27); 3.36 (dd, J=5 and 12 Hz, 1H, H-3); 3.73 (m, 2H, H-21); 5.12 (m, 1H, H-24); 5.55 (m, 1H, H-7); 5.91 (d, J=6 Hz, 1H, H-6)

g) 4,4-Dimethyl-3β-[[dimethyl(1,1-dimethylethyl)silyl]oxy]cholesta-5,7,24-trien-21-ol-methanesulfonate At 0° C., 7.9 ml of methanesulfonic acid chloride is added in drops to a solution of 36.5 g of the compound, described in step f), in a mixture of 155 ml of dichloromethane and 30 ml of triethylamine. After three hours at room temperature, it is dispersed between water and dichloromethane. After the organic phase is washed with sodium bicarbonate solution, saturated common salt solution, drying on sodium sulfate, filtration and concentration by evaporation of the filtrate, 47.4 g of crude 4,4-dimethyl-3β-[[dimethyl(1,1-dimethylethyl)silyl]oxy]cholesta-5,7,24-trien-21-ol-methanesulfonate is obtained, which is further used without purification.

$^1$H-NMR (CDCl$_3$): δ=0.04 ppm (s, 3H, Si—CH$_3$); 0.06 ppm (s, 3H, Si—CH$_3$); 0.62 ppm (s, 3H, H-18); 0.89 ppm (s, 9H, Si-$^t$Bu); 0.97 (s, 3H, H-19); 1.09 (s, 3H, 4-CH$_3$); 1.12 (s, 3H, 4-CH$_3$); 1.61 and 1.70 (1s br. each, in each case 3H, H-26 and H-27); 3.02 (s, 3H, OSO$_2$—CH$_3$); 3.36 (dd, J=5 and 12 Hz, 1H, H-3); 4.24 (dd, J=5 and 10 Hz, 1H, H-21); 4.39 (dd, J=3 and 10 Hz, 1H, H-21); 5.09 (m, 1H, H-24); 5.55 (m, 1H, H-7); 5.91 (d, J=6 Hz, 1H, H-6)

h) 4,4-Dimethyl-3β-[[dimethyl(1,1-dimethylethyl)silyl]oxy]cholesta-5,7,24-triene 47.4 g of the crude product of step g) is reacted according to the method that is described in step f). After the crude product is chromatographed on silica gel with n-hexane as an eluant, 31 g of 4,4-dimethyl-3β-[[dimethyl(1,1-dimethylethyl)silyl]oxy]cholesta-5,7,24-triene is obtained.

$^1$H-NMR (CDCl$_3$): δ=0.04 ppm (s, 3H, Si—CH$_3$); 0.06 ppm (s, 3H, Si—CH$_3$); 0.60 ppm (s, 3H, H-18); 0.90 ppm (s, 9H, Si-$^t$Bu); 0.98 (d, J 7 Hz, 3H, H-21); 0.99 (s, 3H, H-19); 1.10 (s, 3H, 4-CH$_3$); 1.13 (s, 3H, 4-CH$_3$); 1.60 and 1.70 (1s br. each, in each case 3H, H-26 and H-27); 3.35 (dd, J=5 and 12 Hz, 1H, H-3); 5.10 (m, 1H, H-24); 5.53 (m, 1H, H-7); 5.90 (d, J=6 Hz, 1H, H-6)

i) 4,4-Dimethyl-5α-cholesta-8,14,24-trien-3β-ol 22 g of the compound that is described in step h) is boiled in 2.2 liters of 1,4-dioxane with 110 ml of 6N sulfuric acid for 170 hours. After substantial removal of the solvent, the evaporation residue is dispersed between sodium bicarbonate solution and ethyl acetate. After the organic phase is washed with sodium bicarbonate solution and saturated common salt solution, drying on sodium sulfate, filtration and concentration by evaporation, the evaporation residue is chromatographed on silica gel with a mixture of hexane and ethyl acetate. After the eluate is concentrated by evaporation and the evaporation residue is crystallized from ethanol, 4.3 g of 4,4-dimethyl-5-cholesta-8,14,24-trien-3β-ol is obtained in 90% purity. Rechromatography of the mother liquors, concentration by evaporation of the eluate and crystallization of the evaporation residue from a methanol-water mixture produce another 3.8 g of 4,4-dimethyl-5α-cholesta-8,14,24-trien-3β-ol.

Ultimately, 8.1 g (20 mmol) of 4,4-dimethyl-5α-cholesta-8,14,24-trien-3β-ol is obtained.

The NMR data are identical to those of the literature (J. Am. Chem. Soc. 111, 1989, 278).

Example 2

(Process Variant 1)

a) 4,4-Dimethyl-3β-hydroxypregna-8,14-dienoic-21-acid methyl ester 300 g of the compound that is described in Example 1, step d), is boiled in a mixture of 2.7 liters of methanol and 0.4 liter of concentrated hydrochloric acid for 20 hours. After cooling in an ice bath, crystallizate is suctioned out, the filtrate is dispersed between dichloromethane and water, and the organic phase is washed neutral with water. After washing with saturated common salt solution, drying on sodium sulfate and filtration, it is concentrated by evaporation and separated from silanols with a filter column. The crystallizate is washed with water and dried. 125 g of crystallizate and 96 g of mother liquor are obtained. The crystallizate is again boiled in a mixture of 1.2 liters of methanol and 0.2 liter of concentrated hydrochloric acid for 24 hours. After the filtration of the cooled reaction mixture, it is filtered, the mother liquor is washed, dried and concentrated by evaporation. 77 g of crystallizate and 46 g of mother liquor are obtained. Chromatography of the mother liquors that are thus obtained and the second crystallizate on silica gel with a mixture of n-hexane and ethyl acetate produce 92 g of 4,4-dimethyl-3β-hydroxypregna-8,14-dienoic-21-acid methyl ester.

b) 4,4-Dimethyl-3β-[[dimethyl(1,1-dimethylethyl)silyl]oxy]pregna-8,14-dienoic-21-acid methyl ester 92 g of the compound that is described in step a) is stirred with 0.75 liter of N,N-dimethylformamide, 51 g of tert-butyldimethylsilyl chloride and 27.8 g of imidazole for 18 hours at 70° C. After cooling, it is poured onto 10 liters of an ice-cold 0.5 molar aqueous hydrochloric acid and filtered. The filter cake is taken up in ethyl acetate, washed neutral with 1N sodium hydroxide solution, dried on sodium sulfate, filtered and concentrated by evaporation. 124.8 g of 4,4-dimethyl-3β-[[dimethyl(1,1-dimethylethyl)silyl]oxy]pregna-8,14-dienoic-21-acid methyl ester is obtained, which is further used without purification.

c) 4,4-Dimethyl-3β-[[dimethyl(1,1-dimethylethyl)silyl]oxy]-5β-cholesta-8,14,24-trienoic-21-acid methyl ester 123.5 g of the compound that is described in step b), dissolved in 2.0 liters of tetrahydrofuran, is added in drops to a solution of 1.04 mol of lithium diisopropylamide, produced from 652 ml of a 1.6 molar solution of n-butyllithium in hexane and 174 ml of diisopropylamine in 320 ml of tetrahydrofuran at −20° C. After 40 minutes of stirring at 0° C., it is cooled to −10° C., and 270 g of 5-iodo-2-methyl-2-pentene is added in drops. After three hours of stirring at 0° C., the batch is dispersed between ethyl acetate and saturated ammonium chloride solution. After the organic phase is washed with water and saturated common salt solution, drying on sodium sulfate and filtration, it is concentrated by evaporation and coarse-filtered on silica gel with a mixture of n-hexane and ethyl acetate. 113 g (0.2 mol) of 4,4-dimethyl-3β-[[dimethyl(1,1-dimethylethyl)silyl]oxy]-5α-cholesta-8,14,24-trienoic-21-acid methyl ester is obtained, which is further used without purification.

d) 4,4-Dimethyl-3β-[[dimethyl(1,1-dimethylethyl)silyl]oxy]-5α-cholesta-8,14,24-trien-21-ol 112.5 g of the compound that is described in step c), dissolved in 0.7 liter of tetrahydrofuran, is added in drops to 15.04 g of lithium aluminum hydride, suspended in 0.7 liter of tetrahydrofuran at 0° C. After 3 hours of stirring at room temperature, it is mixed with 60 ml of saturated ammonium chloride solution while being cooled with ice. After 20 minutes of stirring, it is mixed with sodium sulfate and suctioned off after another 10 minutes. The evaporation residue is filtered on a short column with dichloromethane as a solvent. After the eluate is concentrated by evaporation, 103.2 g of 4,4-dimethyl-3β-[[dimethyl(1,1-dimethylethyl)silyl]oxy]-5α-cholesta-8,14,24-trien-21-ol is obtained, which is further used without further purification.

e) 4,4-Dimethyl-3β-[[dimethyl(1,1-dimethylethyl)silyl]oxy]-5α-cholesta-8,14,24-trien-21-ol-methanesulfonate At 0° C., 21.8 ml of methanesulfonic acid chloride is added in drops to a solution of 102.3 g of the compound, described in step d), in a mixture of 440 ml of dichloromethane and 84 ml of triethylamine. After three hours at room temperature, it is dispersed between water and dichloromethane. After the organic phase is washed with sodium bicarbonate solution, saturated common salt solution, drying on sodium sulfate, filtration and concentration by evaporation, it is chromatographed on silica gel with a mixture of hexane and ethyl acetate. 78.2 g of 4,4-dimethyl-3□-[[dimethyl(1,1-dimethylethyl)silyl]oxy]-5□-cholesta-8,14,24-trien-21-ol-methanesulfonate is obtained.

f) 4,4-Dimethyl-3β-[[dimethyl(1,1-dimethylethyl)silyl]oxy]-5α-cholesta-8,14,24-triene 77.2 g of the compound that is described in step e) is reacted according to the method that is described in step d). After the crude product is filtered on silica gel with a mixture of n-hexane and ethyl acetate, 63 g of 4,4-dimethyl-3β-[[dimethyl(1,1-dimethylethyl)silyl]oxy]-5α-cholesta-8,14,24-triene is obtained.

g) 4,4-Dimethyl-5α-cholesta-8,14,24-trien-3β-ol 2 g of the compound that is described in step f) is stirred in a mixture of 5 ml of 6N hydrochloric acid, 10 ml of ethanol and 30 ml of tetrahydrofuran for 24 hours at room temperature. Then, it is dispersed between ethyl acetate and water. After the organic phase is washed with 1N sodium hydroxide solution, water and saturated common salt solution, drying on sodium sulfate and filtration, the evaporation residue is chromatographed on silica gel with a mixture of n-hexane and ethyl acetate. 1.45 g of 4,4-dimethyl-5α-cholesta-8,14,24-trien-3β-ol is obtained.

The NMR data are identical to those of the literature (J. Am. Chem. Soc, 111, 1989, 278).

What is claimed is:

1. A process for the production of 4,4-dimethyl-5α-cholesta-8,14,24-trien-3β-ol of formula 1

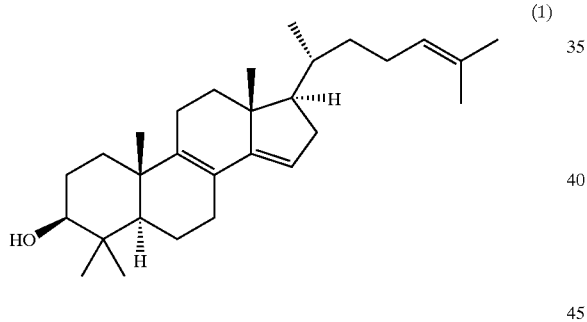
(1)

comprising:

a) reacting a 3-oxopregn-4-enoic-21-acid ester of formula 2

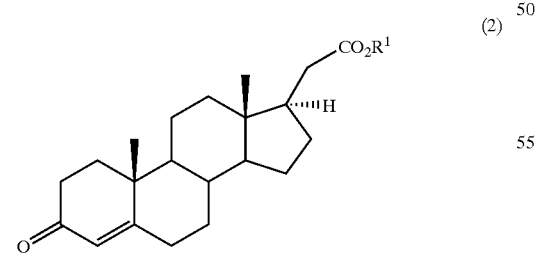
(2)

in which
R$^1$ means hydrogen, branched or unbranched C$_1$–C$_6$ alkyl; phenyl; benzyl; ortho-, meta- or para-methylphenyl, in the presence of a base and a methylating agent to produce a compound of formula 3

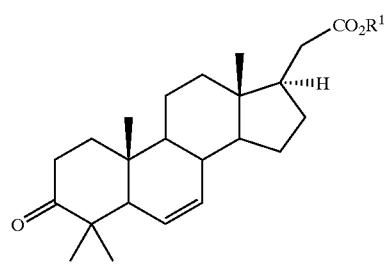
(3)

in which
R$^1$ has the above-mentioned meaning, b) reducing the compound of formula 3 to a compound of formula 4

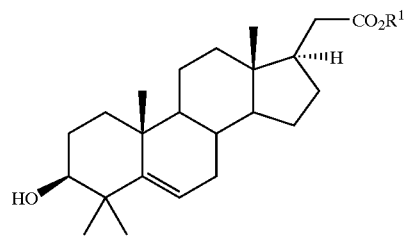
(4)

in which
R$^1$ has the above-mentioned meaning, c) converting the 3-hydroxy group of the compound of formula 4 into a 3-protected hydroxy group of the compound of formula 5

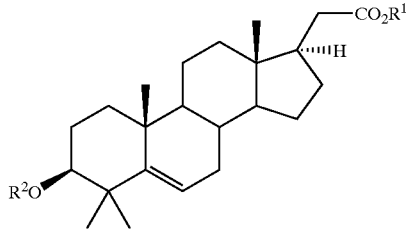
(5)

in which
R$^1$ has the above-mentioned meaning, and
R$^2$ means hydrogen, an ester of an aliphatic or an aromatic carboxylic acid, an acetal protective group, or a silyl ether, d) dehydrogenating the compound of formula 5 into a compound of formula 6

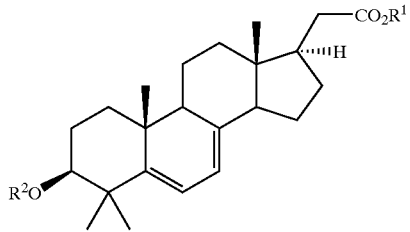
(6)

in which

R¹ and R² have the above-mentioned meanings, e) isomerizing the compound of formula 6 into a compound of formula 7

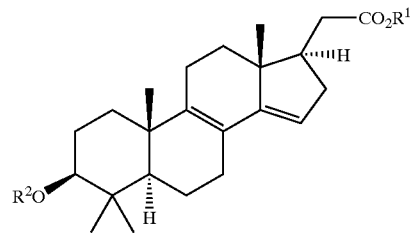

(7)

in which

R¹ and R² have the above-mentioned meaning, f) alkylating the compound of formula 7 into a compound of formula 8

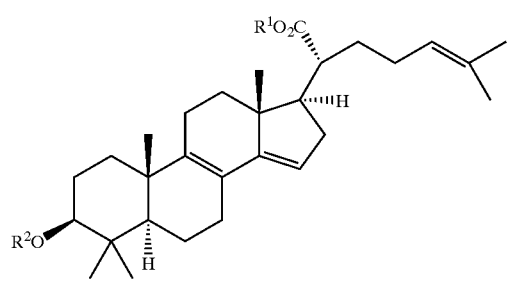

(8)

in which

R¹ and R² have the above-mentioned meaning, g) reducing the ester of the compound of formula 8 into a hydroxymethyl group of a compound of formula 9

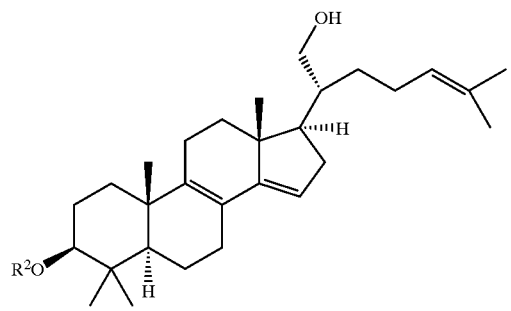

(9)

in which

R² has the above-mentioned meaning, h) converting the primary hydroxyl group in a leaving group of the compound of formula 9 into a compound of formula 10

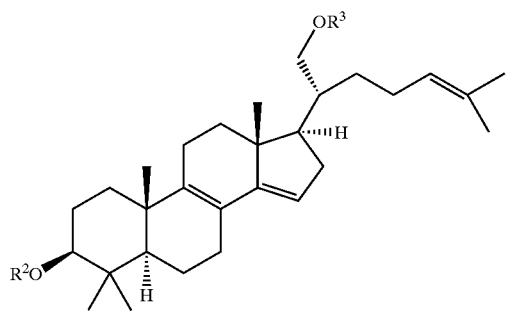

(10)

in which

R² has the above-mentioned meaning, and

R³ stands for radical SO₂R⁴, whereby R⁴ means branched or unbranched $C_1$–$C_6$ alkyl; phenyl; benzyl; ortho-, meta- or para-methylphenyl or 2,4,6-trimethylphenyl, and, if R² is hydrogen, the direct reaction of a compound of formula 10 into 4,4-dimethyl-5α-cholesta-8,14,24-trien-3β-ol of formula 1, i) or if R² is a protective group by reductive removal of the —OR³ grouping into a compound of formula 11

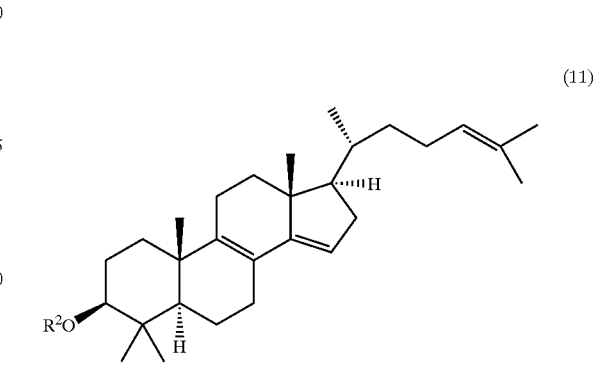

(11)

in which

R² has the above-mentioned meaning, and and cleavage of the protective group.

2. A process for the production of 4,4-dimethyl-5α-cholesta-8,14,24-trien-3β-ol of formula 1,

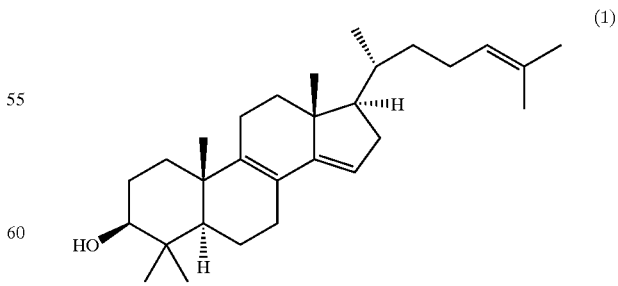

(1)

comprising:

a) alkylating a compound of formula 6 according to claim 1

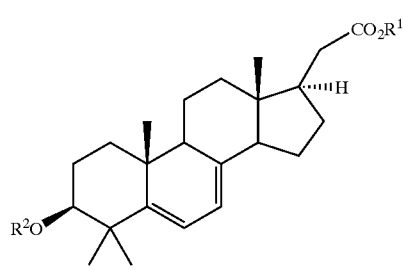

(6)

in which

R$^1$ means hydrogen, branched or unbranched C$_1$–C$_6$ alkyl; phenyl; benzyl; ortho-, meta- or para-methylphenyl, R$^2$ means hydrogen, an ester of an aliphatic or an aromatic carboxylic acid, an acetal protective group, or a silyl ether, to produce a compound of formula 12

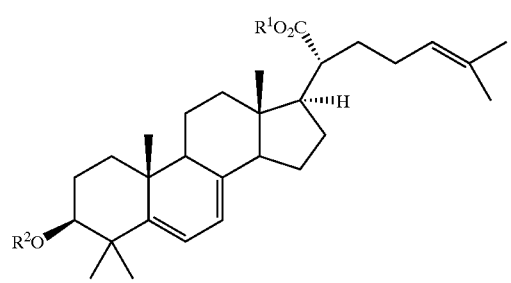

(12)

in which

R$^1$ and R$^2$ have the above-mentioned meanings, b reducing the ester group into a hydroxymethyl compound of formula 13

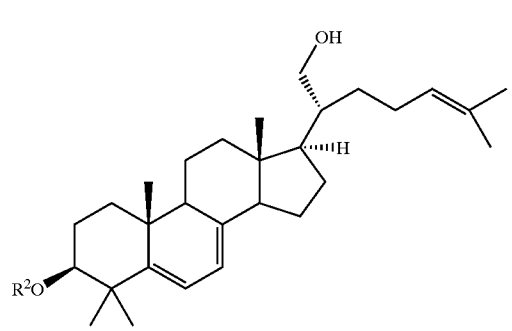

(13)

in which

R$^1$ has the above-mentioned meaning, c converting a primary hydroxyl group in a leaving group into a compound of formula 14

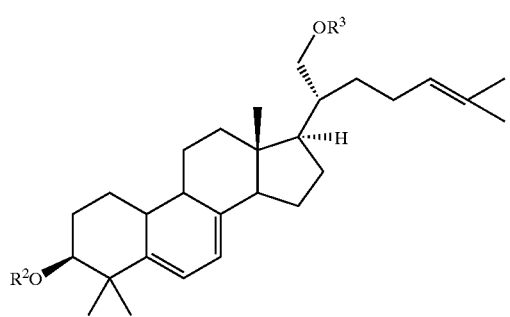

(14)

in which

R$^1$ and R$^2$ have the above-mentioned meanings, d reductively removing the —OR$^3$ grouping to produce a compound of formula 15

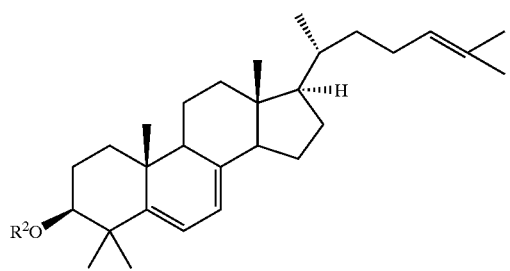

(15)

in which

R$^2$ has the above-mentioned meaning, and if R$^2$ is hydrogen, the direct reaction of a compound of formula 10 into 4,4-dimethyl-5α-cholesta-8,14,24-trien-3β-ol of formula 1, or, if R$^2$ is a protective group, e isomerizing to produce a compound of formula 11

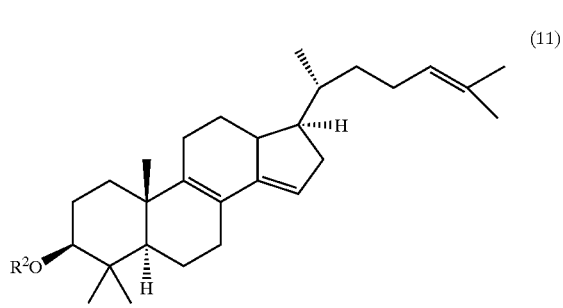

(11)

in which

R$^2$ has the above-mentioned meaning, and cleavage of the protective group.

3. A process for the production of 4,4-dimethyl-5α-cholesta-8,14,24-trien-3β-ol of formula 1

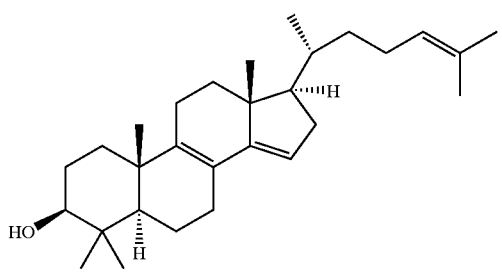
(1)

comprising:

isomerizing a compound of formula 6

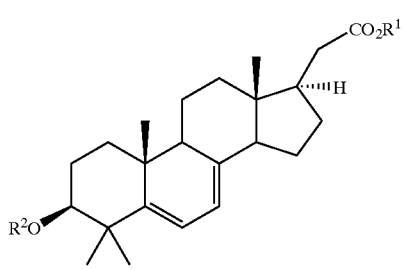
(6)

$R^1$ means hydrogen, branched or unbranched $C_1$–$C_6$ alkyl; phenyl; benzyl; ortho-, meta- or para-methylphenyl, $R^2$ means hydrogen, an ester of an aliphatic or an aromatic carboxylic acid, an acetal protective group, or a silyl ether.

4. A process for the production of 4,4-dimethyl-5α-cholesta-8,14,24-trien-3β-ol of formula 1

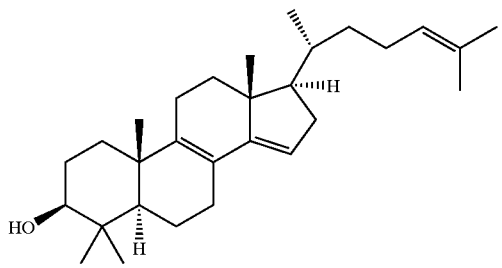
(1)

comprising:

dehydrogenating a compound of formula 5:

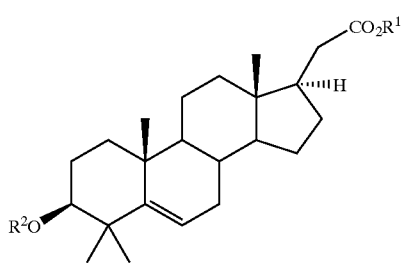
(5)

to produce a compound of formula 6

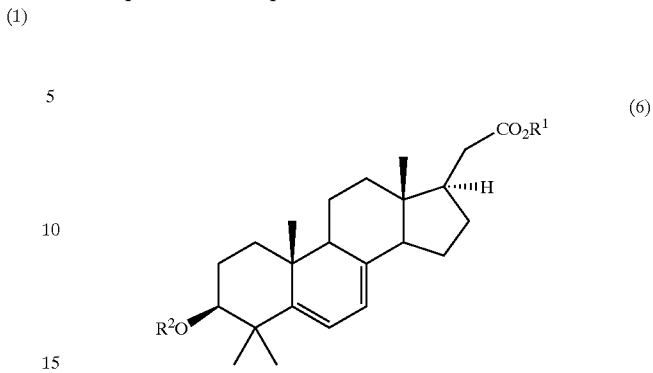
(6)

$R^1$ means hydrogen, branched or unbranched $C_1$–$C_6$ alkyl; phenyl; benzyl; ortho-, meta- or para-methylphenyl, $R^2$ means hydrogen, an ester of an aliphatic or an aromatic carboxylic acid, an acetal protective group, or a silyl ether.

5. A process for the production of 4,4-dimethyl-5α-cholesta-8,14,24-trien-3β-ol of formula 1,

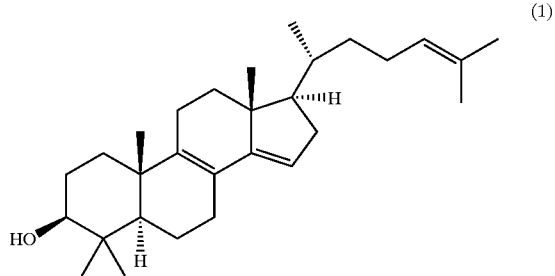
(1)

comprising:

a) alkylating a compound of formula 6 according to claim 1

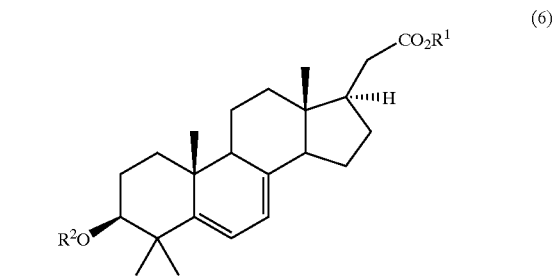
(6)

in which $R^1$ means hydrogen, branched or unbranched $C_1$–$C_6$ alkyl; phenyl; benzyl; ortho-, meta- or para-methylphenyl, $R^2$ means hydrogen, an ester of an aliphatic or an aromatic carboxylic acid, an acetal protective group, or a silyl ether, to produce a compound of formula 12
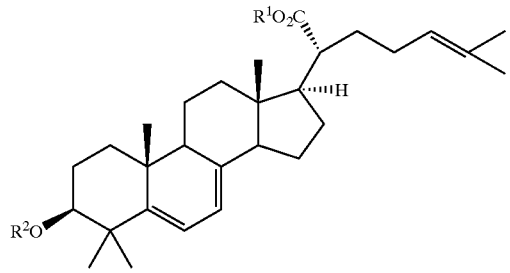
in which
R¹ and R² have the above-mentioned meanings.
6. Compounds of general formula 6
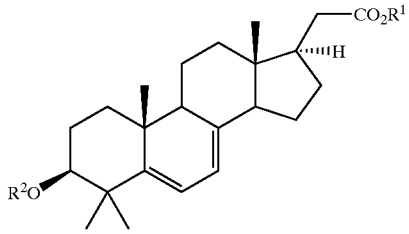
(6)
in which
R¹ means hydrogen, branched or unbranched $C_1$–$C_6$ alkyl; phenyl; benzyl; ortho-, meta- or para-methylphenyl and
R² means hydrogen, esters of aliphatic and aromatic carboxylic acids, or silyl ethers.
* * * * *

UNITED STATES PATENT AND TRADEMARK OFFICE
CERTIFICATE OF CORRECTION

PATENT NO. : 6,683,197 B1
DATED : January 27, 2004
INVENTOR(S) : Thorsten Blume et al.

It is certified that error appears in the above-identified patent and that said Letters Patent is hereby corrected as shown below:

<u>Title page, Item [54] and Column 1, lines 2 and 3</u>,
Title, reads "DIMETHYL-5αA-" should read -- DIMETHYL-5α- --; and "3β-01" should read -- 3β-OL --

<u>Column 16,</u>
Line 26, reads "or if" should read -- or, if --
Line 26, reads "protective group by" should read -- protective group, by --
Line 47, reads "and and" should read -- and --

<u>Column 17,</u>
Line 44, reads "b reducing" should read -- b) reducing --
Line 66, reads "c converting" should read -- c) converting --

<u>Column 18,</u>
Line 20, reads "d reductively" should read -- d) reductively --
Line 47, reads "e isomerizing" should read -- e) isomerizing --

Signed and Sealed this

Twenty-first Day of December, 2004

JON W. DUDAS
*Director of the United States Patent and Trademark Office*